United States Patent [19]

Nagy née Kricsfalussy et al.

[11] Patent Number: 4,661,340

[45] Date of Patent: Apr. 28, 1987

[54] QUAIL EGG BASED STABILIZED FOAM COMPOSITIONS FOR COSMETIC PURPOSES

[75] Inventors: Margit Nagy née Kricsfalussy; Anna Závodszky née Szabó; József Rákóczi; József Halmos, all of Budapest, Hungary

[73] Assignee: Interkémia Vegyipari Gazdasági Társaság, Budapest, Hungary

[21] Appl. No.: 641,120

[22] Filed: Aug. 15, 1984

Related U.S. Application Data

[63] Continuation-in-part of Ser. No. 511,424, Jun. 6, 1983, abandoned.

[51] Int. Cl.[4] .......................... A61K 7/42; A61K 7/46; A61K 7/48; A61K 9/12
[52] U.S. Cl. .......................................... 424/47; 424/59; 424/60; 424/63; 424/70; 514/776; 514/844; 514/847
[58] Field of Search ...................... 424/45, 59, 70, 63, 424/47, 60; 514/776

[56] References Cited

U.S. PATENT DOCUMENTS

| | | | |
|---|---|---|---|
| 376,808 | 1/1888 | Pratt | 424/70 X |
| 1,566,271 | 12/1925 | Cesa | 424/359 |
| 1,924,972 | 8/1933 | Beckert et al. | 424/359 X |
| 2,100,090 | 11/1937 | Sommer et al. | 424/70 X |
| 3,483,008 | 12/1969 | Herr | 424/65 X |

FOREIGN PATENT DOCUMENTS 13640 of 1913 United Kingdom ................ 424/70

OTHER PUBLICATIONS

Chem. Abstracts, 1967, vol. 66, 98435f & 98436g.
Merck Index, Ninth Edition, 9377, p. 1246.
Chem. Abs., 1970, vol. 73, p. 128136y.

Primary Examiner—Dale R. Ore
Attorney, Agent, or Firm—Gabriel P. Katona

[57] ABSTRACT

According to the invention there are provided a quail egg based stabilized foam composition for cosmetic purposes comprising 5-75% by weight of quail egg, 20-80% by weight of one or more carrier/s/, 0-40% by weight of one or more additive/s/, 0.1-1% by weight of one or more antiseptic agent/s/ and 1-3% by weight of one or more sulfonamide/s/ potentiated with 2,4-diamino-5-/3',4',5'-trimethoxybenzyl/pyrimidine in a weight ratio of /1:5/-/5:1/, furthermore 5-20% by weight of a propellant.

The compositions of the present invention can be stored for a very long period of time without decomposition due to their excellent stability.

2 Claims, No Drawings

QUAIL EGG BASED STABILIZED FOAM COMPOSITIONS FOR COSMETIC PURPOSES

TECHNICAL FIELD

The invention relates to quail egg based stabilized foam compositions for cosmetic purposes.

BACKGROUND ART

In the last 10-15 years body conditioning requisites, in which a substance of natural origin is responsible for the cosmetic effect, have become much sought. Thus, cosmetic compositions—particularly creams—comprising collagen, placenta extract, etc. are known.

It is preferred to apply a cosmetic composition as a foam to the skin [Chemical Abstracts, 66, 98436 g /1967/].

Cosmetic compositions prepared from hen egg are known [U.S. Pat. Nos. 376 808; 1 566 271; 1 924 972; 2 100 090 and 3 483 008]. However, it is also known that the cosmetic effect of quail egg is superior to that of hen egg since the former has higher egg yolk, dry matter and fat contents [Chemical Abstracts, 79, 77108e /1973/]. Especially the calcium, phosphorus, molybdenum, vitamin A and phospholipid /chiefly lecithin/ contents are high [ibid]. The considerable vitamin A contents are important in the treatment of persons suffering in vitamin A deficiency leading to dry skin. The cosmetic effect of lecithin is extremely valuable since this substance has an effect on the permeability of cell walls and favours the absorption of active substances. Thus, the biologically active substances of the quail egg are completely absorbed.

Furthermore, quail egg comprises higher levels of trace elements such as iron, zinc, copper, rhodium, titanium, cobalt, vanadium, calcium, manganese, sodium, tantalum, phosphorus and magnesium [Chemical Abstracts, 76, 97080f /1972/].

In addition, quail egg contains higher amounts of amino acids such as tyrosine, threonine, serine, lysine, glycine and histidine than hen egg does. Of the amino acids present in quail egg, tyrosine is very important as it plays a significant role in the metabolism and favours the pigment formation, thus, the appearance of a healthy skin color.

Therefore, in cosmetic treatments skin conditioning packs made from quail egg are often used. Quail eggs are opened immediately before use and the fluid thereof is incorporated into the mass which is applied onto the face to be treated with the aid of conventional carriers generally used in cosmetic industry. The face-skin conditioning pack thus obtained exhibits favourable biological effects, however, it cannot be stored, is liable to quick decomposition since it constitutes an excellent nutrient medium for microbes. Furthermore, the pack obtained cannot be exactly reproduced. The unopened quail eggs are relatively unfavourably storable, too, and cannot be stored even in a refrigerator for a longer period of time.

The further characteristics of domestically made cosmetic compositions /consistence, color, odor, etc./ do not comply with the requirements raised against up-to-date cosmetic compositions. Due to the fact that preservation remained unsolved, quail egg based cosmetic compositions failed to appear on the market and the use of crude quail egg for cosmetic purposes did not become widespread.

According to Hungarian patent No. 174 863 transitional preservation of hen's egg is carried out by adding potassium sorbate and adjusting the pH to a value between 4.8 and 5.4. The egg-fluid thus obtained can be stored at 4°-8° C. but it is unsuitable for storage at a higher temperature or a longer period of time.

We have tried to preserve natural quail egg-fluid according to the process described in Hungarian Pat. No. 174 863, but the results obtained were still more unfavourable. After two or three days the egg-fluid had a bad smell and became completely unsuitable for cosmetic purposes.

It is known that cosmetic compositions are preserved by means of antiseptic agents. In our experiments, cosmetic carriers and additives were mixed with quail egg-fluid is 4% by weight of one or more known antiseptic agent/s/ such as boric acid, sorbic acid, benzoic acid, salicylic acid, p-hydroxybenzoic acid, alkyl or benzyl p-hydroxybenzoate and/or beta-phenylalkanol were added. The compositions obtained could be stored for only 1 to 3 weeks without decomposition. Thus, the conventional cosmetic stabilizers have not been sufficient for the preservation of the cosmetic preparations based on quail egg.

It is also known that bacterial growth is inhibited by sulfonamides, and this effect is higher in cases of sulfonamides potentiated with 2,4-diamino-5/-3',4',5'-trimethoxybenzyl/pyrimidine/trimethoprim/ having antibacterial effect in itself, too [Chemical Abstracts, 73, 128136y /1970/; The Merck Index, Ninth Edition, 9377, p. 1246, Meck and Co., Inc., Rahway, N.J., USA]. Therefore, the above experiments were repeated using 4% by weight of sulfonamide/s/, trimethoprim and sulfonamide/s/ potentiated with trimethoprim, respectively. However, even these very active antibacterial agents could not insure preservation for a longer period than 4 to 12 weeks. Then the components of quail egg began to decompose.

Such a short term preservation is not sufficient for a cosmetic composition. Preservation for at least one year or preferably for a still longer time is necessary.

DISCLOSURE OF THE INVENTION

The object of the invention is to provide quail egg based foam compositions for cosmetic purposes, in which the valuable biological effects of the nutrient components being present in the quail egg are accompanied by suitable stability and storability.

According to the present invention there are provided stabilized and excellently storable quail egg based foam compositions for cosmetic purposes which comprise 5-75% by weight of quail egg, 20-80% by weight of one or more carrier/s/, 0-40% by weight of one or more additives/s/, 0.1-1% by weight of one or more antiseptic agent/s/ and 1-3% by weight of one or more sulfonamide potentiated with trimethoprim in a weight ratio of /1:5/-/5:1/, furthermore 5-20% by weight of a propellant.

The foam compositions of the invention were examined for stability as follows:

55 parts by weight of natural quail egg-fluid, 1.26 parts by weight of stearic acid, 0.308 parts by weight of myristic acid, 1.232 parts by weight of triethanol amine, 1.12 parts by weight of glycerol, 19.68 parts by weight of water is 0.1 parts by weight of odorant were mixed as described in Example 1. To the emulsion obtained, the mixture of stabilizers given in Table I, 2 parts by weight of water and 0.6 parts by weight of polyoxy ethylene glycol /molecular weight: 300/ were added. The emulsion obtained was filled into aerosol flasks, which were hermetically closed and 14.8 parts by weight of propellant were introduced. The flasks were stored at 25° C. and foam samples were taken once every week. The consistence and odor of the foam samples were controlled. A loose foam that becomes liquid and the bad smell of decomposed egg indicate the lack of stability of the emulsion present in the flasks.

The qualitative and quantitative composition of the stabilizers as well as the stability period of the emulsion are given in Table I. The cosmetic compositions tested were stored until the end of stability or at most for 2 years, if they were still stable at the end of the second year.

TABLE I

| Stabilizer | | |
|---|---|---|
| type | amount in parts by weight | Stability period in weeks |
| boric acid | 4 | 1 |
| sorbic acid | 4 | 1 |
| benzoic acid | 4 | 1 |
| p-hydroxybenzoic acid | 4 | 1 |
| methyl p-hydroxybenzoate | 4 | 2 |
| salicylic acid | 4 | 2 |
| ethyl p-hydroxybenzoate | 4 | 2 |
| propyl p-hydroxybenzoate | 4 | 3 |
| butyl p-hydroxybenzoate | 4 | 2 |
| benzyl p-hydroxybenzoate | 4 | 2 |
| beta-phenylethanol | 4 | 3 |
| beta-phenylpropanol | 4 | 4 |
| beta-phenylbutanol | 4 | 2 |
| boric acid | 2 | 2 |
| beta-phenylethanol | 2 | |
| methyl p-hydroxybenzoate | 1 | 3 |
| beta-phenylpropanol | 3 | |
| trimethoprim | 4 | 4 |
| sulfamethoxazole | 4 | 5 |
| sulfa-methoxypyridazine | 2 | 5 |
| sulfamethoxazole | 2 | |
| sulfa-chloropyridazine | 4 | 4 |
| trimethoprim | 1 | 8 |
| sulfadiazine | 3 | |
| sulfadimidine | 2 | |
| sulfa-methoxydiazine | 2.2 | 12 |
| trimethoprim | 0.8 | |
| sulfathiourea | 4 | 2 |
| sulfaguanidine | 4 | 6 |
| trimethoprim | 0.7 | 12 |
| sulfamethoxazole | 3.3 | |
| trimethoprim | 3 | 10 |
| sulfa-chloropyridazine | 1 | |
| boric acid | 0.3 | |
| beta-phenylethanol | 0.7 | 104* |
| trimethoprim | 1 | |
| sulfa-chloropyridazine sodium | 2 | |
| sorbic acid | 1 | |
| trimethoprim | 0.5 | 100 |
| sulfamethoxazole | 2.5 | |
| benzoic acid | 0.2 | |
| salicylic acid | 0.8 | 100 |
| trimethoprim | 2.5 | |
| sulfamethoxazole | 0.5 | |
| p-hydroxybenzoic acid | 0.1 | |
| beta-phenylbutanol | 0.9 | 104* |
| trimethoprim | 1.5 | |
| sulfa-methoxypyridazine | 1.5 | |
| methyl p-hydroxybenzoate | 0.5 | |
| beta-phenylpropanol | 0.5 | 104* |
| trimethoprim | 1 | |
| sulfadiazine | 2 | |
| ethyl p-hydroxybenzoate | 1 | |
| trimethoprim | 0.5 | 104 |
| sulfadimidine | 2.5 | |
| propyl p-hydroxybenzoate | 0.1 | |
| boric acid | 0.3 | |
| beta-phenylethanol | 0.6 | 104* |
| trimethoprim | 0.6 | |
| sulfa-methoxydiazine | 0.8 | |

TABLE I-continued

| Stabilizer | | |
|---|---|---|
| type | amount in parts by weight | Stability period in weeks |
| sulfamethoxazole | 1.6 | |
| benzyl p-hydroxybenzoate | 1 | |
| trimethoprim | 2 | 96 |
| sulfathiourea | 1 | |
| salicylic acid | 0.1 | |
| beta-phenylbutanol | 0.3 | |
| methyl p-hydroxybenzoate | 0.6 | 100 |
| trimethoprim | 1.5 | |
| sulfaguanidine | 1.5 | |

*The composition remained stable after 2 years/104 weeks/.

It can be seen from Table I that the stabilizers of the invention insure higher stability with one magnitude of order than the components thereof. Thus, synergism is obtained with the stabilizers of the invention.

Prior to use, the foam composition of the inventon consists of an emulsion to be converted into a foam and a propellant. When the emulsion is expelled from the aerosol flask, it is foamed by the propellant. In this way, the stabilized composition of the invention is applied as a foam to the body surface to be treated. The foam can be easily dispersed on the skin and is absorbed rapidly. The foam compositions of the invention can be used, for example, for the face-skin conditioning of women and men having different skin type, for body conditioning, for sun-bathing, as a shampoo, hair pack or shaving foam. Of course, the different types of foam composition comprise the cosmetic carriers and additives usually employed in the cosmetic composition in question.

The term "quail egg" used throughout the specification relates to eggs of domesticated quails /Coturnix coturnix/ and encompasses all forms of the egg, particularly the substance available after cracking the egg, complete egg /natural egg-fluid/, egg-yolk, egg-white, complete egg enriched with egg-yolk or egg-white; the aforesaid substances may be used either in moist or in liophylized form.

As carrier, the following substances can preferably be used: water; mono- or polyhydric alcohols, e.g., ethanol, cetyl alcohol, octyl-dodecanol, oleyl alcohol, ethylene glycol, polyglycol ether or glycerol; fatty acids, e.g. stearic acid or myristic acid; alkali metal salts of fatty acids; fatty acid esters, e.g. propyl myristate or esters of oleic acid formed with fatty alcohols, etc.; paraffin oil; wax; vaseline; woolfat; etc.

As additives preferably surfactants, odorants, colorants, biologically active substances, light-protecting agents, etc. can be used. The compositions of the invention can contain one or more—i.e. an optional number—of additives, in a total amount of 0–40% by weight.

The surfactants can be of anionic, cationic or nonionic character, e.g. sodium lauryl sulfate, polyoxyethylene fatty acid esters, sorbitan fatty acid esters, polyoxyethylene fatty alcohol ethers, polyoxyethylene sorbitan fatty acid esters, etc.

As odorants and colorants conventional agents generally used in cosmetic compositions can be employed.

In addition to the quail egg, the compositions of the invention may also contain further biologically active substances, such as vitamins, solubilized collagen, camomile extract, placenta extract, etc.

As light protecting agent preferably 2-hydroxy-4-methoxy-benzophenone-5-sulfonic acid can be used.

The stabilizers present in the compositions of the invention consist of 0.1–1% by weight of one or more antiseptic agent/s/ and 1 to 3% by weight of one or more sulfonamide/s/ potentiated with trimethoprim.

Preferred antiseptic agents are boric acid, sorbic acid, benzoic acid, salicylic acid, p-hydroxybenzoic acid, alkyl p-hydroxybenzoate such as methyl p-hydroxybenzoate, ethyl p-hydroxybenzoate, propyl p-hydroxybenzoate and butyl p-hydroxybenzoate, benzyl p-hydroxybenzoate and/or beta-phenylalkanol such as beta-phenylethanol, beta-phenylpropanol or beta-phenylbutanol.

Preferred sulfonamides are $N^1$-/5-methyl-3-isoxazolyl/sulfanylamide/sulfamethoxazole/, $N^1$-/6-chloro-3-pyridazinyl/sulfanylamide/sulfa-chloropyridazine/, $N^1$-/6-methoxy-3-pyridazinyl/-sulfanylamide/sulfa-methoxypyridazine/, $N^1$-/2-pyrimidinyl/-sulfanylamide/sulfadiazine/, $N^1$-/4,6-dimethylpyrimidinyl/-sulfanylamide/sulfadimidine/, $N^1$-/5-methoxypyrimidinyl/-sulfanylamide/sulfa-methoxydiazine/, 1-sulfanilylthiourea/sulfathiourea/ and $N^1$-amidinosulfanylamide/sulfaguanidine/, etc.

Of course, both the antiseptic agents and the sulfonamides can be present in the compositions of the invention as salts or acid addition salts thereof.

The propellant can be any conventional propellant /gas or gas mixture/ generally used in aerosol compositions /e.g. fluorinated and/or chlorinated hydrocarbons such as difluoro dichloro methane, tetrafluoro dichloro ethane and mixtures thereof, dinitrogen oxide, etc.

The compositions of the invention are prepared by admixing the components in an optional order of succession. The order of succession of the addition of the components is determined by the properties—particularly the solubility—of the said components and the type of the composition to be prepared. As additive, surfactants formed in situ during the admixture of the components can be applied, too, e.g. surfactants formed from stearic acid and/or myristic acid and triethyl amine by salt formation.

The emulsion thus obtained is filled into aerosol flasks equipped with a valve, then the propellant is introduced into the flask. On pressing the valve, the composition leaves the flask in the form of a foam.

INDUSTRIAL APPLICABILITY

The quail egg based foam compositions of the present invention are valuable cosmetics and can be stored even for years without decomposition or discoloration and keep their microbiological purity.

MODES OF CARRYING OUT THE INVENTION

Further details of the present invention are to be found in the following Examples, without limiting the scope of the invention to the said Examples.

EXAMPLE 1

| Aerosol foam for face-skin conditioning of women | |
|---|---|
| Component | Amount, parts by weight |
| Quail egg/natural egg-fluid/ | 55.000 |
| Stearic acid | 1.260 |
| Myristic acid | 0.308 |
| Triethanol amine | 1.232 |
| Glycerol | 1.120 |
| Water/demineralized by ion exchange/ | 23.580 |
| Odorant | 0.100 |
| beta-phenylethanol | 0.100 |

-continued

| Aerosol foam for face-skin conditioning of women | |
|---|---|
| Component | Amount, parts by weight |
| Methyl p-hydroxybenzoate | 0.100 |
| Trimethoprim | 0.300 |
| Sulfamethoxazole | 1.500 |
| Carbowax/polyoxy ethylene glycol, molecular weight: 300/ | 0.600 |
| Propellant/difluoro dichloro methane/ | 14.800 |
| Total weight | 100.000 |

Myristic acid, stearic acid and isopropyl myristate are melt by heating on a water bath at a temperature of about 70° C. /oil phase/.

Glycerol and triethanol amine are added to the water, the mixture is heated to 60°–70° C., the methyl p-hydroxybenzoate is dissolved and the mixture thus obtained /aqueous phase/ is added in portions under stirring to the still warm melt. The emulsion thus obtained is stirred until it gets cooled, the homogenized natural quail egg-fluid, odorant, beta-phenylethanol and the solution of trimethoprim and sulfonamide formed with 0.6 g of Carbowax 300 and 0.4 g of water are added in succession and in portions. The emulsion thus obtained is filled into aerosol flasks which are hermetically closed and the propellant is introduced. The composition obtained can be stored for a longer time than two years.

EXAMPLE 2

| Aerosol foam for face-skin conditioning of men | |
|---|---|
| Component | Amount, parts by weight |
| Quail egg/lyophilized/complete egg-fluid/ | 21.50 |
| Myristic acid | 0.48 |
| Stearic acid | 1.95 |
| Olive oil | 21.50 |
| Triethanol amine | 1.90 |
| Isopropyl myristate | 0.67 |
| Distilled water | 33.50 |
| Odorant | 0.10 |
| beta-Phenylpropanol | 1.00 |
| Methyl p-hydroxybenzoate | 0.50 |
| Carbowax 300 | 3.60 |
| Trimethoprim | 0.30 |
| Sulfa-chloropyridazine | 1.50 |
| Propellant | 12.00 |
| Total weight | 100.00 |

One proceeds as described in Example 1. The olive oil is treated as a component of the oil phase. The lyophilized egg is admixed with half amount of the water and the mass thus obtained is added to the emulsion under stirring. The trimethoprim and the sulfa-chloropyridazine are dissolved in a 5:2 mixture of Carbowax 300 and water and this solution is added to the emulsion.

The composition obtained can be stored for a longer period than two years.

EXAMPLE 3

| Body conditioning aerosol foam | |
|---|---|
| Component | Amount parts by weight |
| Quail egg/lyophilized egg-fluid enriched with egg-yolk/ | 10.00 |
| Wool-fat | 1.65 |
| Stearic acid | 1.10 |

Body conditioning aerosol foam

| Component | Amount parts by weight |
| --- | --- |
| Emulgade 1000/a mixture of 80% of saturated fatty alcohol and 20% of fatty alcohol polyglycol ether/ | 2.00 |
| Propylene glycol | 2.15 |
| Triethanol amine | 0.50 |
| Glycerol | 2.00 |
| Collagen/solubilized/ | 3.00 |
| Odorant | 0.60 |
| Distilled water | 47.40 |
| beta-Phenylethanol | 0.60 |
| Sorbic acid | 3.00 |
| Carbowax 300 | 6.00 |
| Trimethoprim | 2.00 |
| Sulfa-chloropyridazine | 1.00 |
| Propellant | 17.00 |
| Total weight | 100.00 |

The wool-fat, stearic acid and emulsifier /Emulgade 1000/ are melt at 60°–70° C. /oil phase/.

The propylene glycol, glycerol and triethanol amine are added to half amount of the water and the mixture is heated near to boiling. The aqueous phase thus obtained is added to the still warm oil phase under stirring and the emulsion is cooled under stirring. To the cold emulsion the collagen and the further components are added and the mixture thus obtained is worked up as described in Example 1 or 2.

The composition obtained can be stored for a longer period than two years.

EXAMPLE 4

Aerosol foam for shampoo and hair pack

| Component | Amount parts by weight |
| --- | --- |
| Quail egg/lyophilized egg-fluid enriched with egg-white/ | 10.00 |
| Tego-Betain L7/fatty acid amino alkyl betaine/ | 15.00 |
| Polyvinyl pyrrolidone | 0.50 |
| Fenopon TC42/sulfoalkyl amide/ | 17.00 |
| Distilled water | 34.55 |
| Odorant | 0.50 |
| beta-Phenylethanol | 1.00 |
| Carbowax 300 | 2.10 |
| Trimethoprim | 1.05 |
| Sulfachloropyridazine | 1.30 |
| Propellant | 17.00 |
| Total weight | 100.00 |

The polyvinyl pyrrolidone, Tego-Betain L 7 and Fenopon TC42 are dissolved in half amount of the water at 60°–70° C. After cooling, the lyophilized egg-fluid and other components admixed with the remaining part of water are added under slow stirring. Further on one proceeds as described in Example 1 or 2. The composition obtained can be stored for a longer period than two years.

EXAMPLE 5

Aerosol foam for sun-bathing

| Component | Amount parts by weight |
| --- | --- |
| Quail egg/natural egg-fluid/ | 15.00 |
| Triethanol amine | 3.43 |
| Sorbitol/70% solution/ | 3.43 |
| Carbopol 934/polyacrylic acid/ | 0.10 |
| Wool-fat | 1.36 |
| Isopropyl myristate | 1.60 |
| Cetyl alcohol | 0.15 |
| Stearic acid | 4.15 |
| Distilled water | 42.38 |
| 2-hydroxy-4-methoxy-benzophenone-5-sulfonic acid | 2.00 |
| Odorant | 0.50 |
| beta-phenylethanol | 0.50 |
| Carbowax 300 | 7.20 |
| Trimethoprim | 0.20 |
| Sulfa-chloropyridazine | 1.00 |
| Propellant | 15.00 |
| Total weight | 100.00 |

The Carbopol 934 and 2-hydroxy-4-methoxy-benzophenone-5-sulfonic acid are dissolved and dispersed, respectively, in a mixture of water, sorbitol and triethanol amine by heating at 60°–70° C. /aqueous phase/.

The wool-fat, isopropyl myristate, cetyl alcohol and stearic acid are melt on a water bath and the aqueous phase having a temperature of 60° C. is added to the melt. After cooling, the further components are added to the emulsion and furtheron one proceeds as described in Example 1 or 2.

The composition obtained can be stored for at least two years.

EXAMPLE 6

Aerosol foam for shampoo

| Component | Amount parts by weight |
| --- | --- |
| Quail egg/lyophilized complete egg-fluid/ | 5.00 |
| Tego-Betain L7 | 18.00 |
| Polyvinyl pyrrolidone | 0.50 |
| Fenopon TC42 | 19.00 |
| Distilled water | 28.90 |
| Odorant | 0.50 |
| Collagen/solubilized/ | 2.00 |
| Boric acid | 1.00 |
| Carbowax 300 | 2.10 |
| Trimethoprim | 0.80 |
| Sulfamethoxazole | 2.20 |
| Propellant | 20.00 |
| Total weight | 100.00 |

One proceeds as described in Example 4.

What we claim is:

1. A stabilized skin and hair treating cosmetic foam composition comprising 5–75% by weight of quail egg, 20–80% by weight of a cosmetically acceptable carrier, 0–40% by weight of a cosmetically acceptable additive selected from the group consisting of a surfactant, odorant, colorant and light protecting agent, 0.1–1% by weight of a cosmetically acceptable antiseptic selected from the group consisting of boric acid, sorbic acid, benzoic acid, salicylic acid, p-hydroxybenzoic acid, propyl p-hydroxybenzoate, benzyl p-hydroxybenzoic acid, methyl p-hydroxybenzoate, benzyl p-hydroxybenzoate, ethyl p-hydroxybenzoate, beta-phenylethanol, beta-phenylpropanol, and beta-phenylbutanol and 1–3% by weight of a sulfonamide which is sulfamethoxazole, sulfa-chloropyridazine, sulfamethoxypyridazine, sulfadiazine, sulfadimidine, sulfa-methoxydiazine, sulfathiourea, and sulfaguanidine, potentiated with trimethoprim in a weight ratio of 1:5 to 5:1, and 5–20% by weight of a propellant.

2. The stabilized composition of claim 1, wherein the carrier is selected from the group consisting of water, monohydric alcohol, polyhydric alcohol, fatty acid, alkali metal salt of fatty acid, fatty acid ester, paraffin oil and wool fat.

* * * * *